United States Patent
Yajima et al.

(10) Patent No.: US 9,901,243 B2
(45) Date of Patent: Feb. 27, 2018

(54) ENDOSCOPE AND ENDOSCOPE SYSTEM (71) Applicant: OLYMPUS CORPORATION, Hachioji-shi, Tokyo (JP)

(72) Inventors: Masanori Yajima, Hachioji (JP); Toru Shinmura, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/200,623

(22) Filed: Jul. 1, 2016

(65) Prior Publication Data
US 2016/0309990 A1 Oct. 27, 2016

Related U.S. Application Data (63) Continuation of application No. PCT/JP2015/063473, filed on May 11, 2015.

(30) Foreign Application Priority Data

Jul. 25, 2014 (JP) ................. 2014-151974

(51) Int. Cl.
*A61B 1/00* (2006.01)
*A61B 1/06* (2006.01)
(Continued)

(52) U.S. Cl.
CPC ...... *A61B 1/00133* (2013.01); *A61B 1/00032* (2013.01); *A61B 1/00068* (2013.01);
(Continued)

(58) Field of Classification Search
CPC .. A61B 1/00068; A61B 1/015; A61B 1/00137
(Continued)

(56) References Cited

U.S. PATENT DOCUMENTS 4,545,369 A * 10/1985 Sato .................. A61B 1/121
600/133
4,667,655 A * 5/1987 Ogiu ................. A61B 1/12
600/132
(Continued)

FOREIGN PATENT DOCUMENTS

JP  2000-157484 A  6/2000
JP  2003-010098 A  1/2003
(Continued)

OTHER PUBLICATIONS

Feb. 9, 2017 International Preliminary Report on Patentability issued in Patent Application No. PCT/JP2015/063473.
(Continued)

*Primary Examiner* — Matthew J Kasztejna
(74) *Attorney, Agent, or Firm* — Oliff PLC (57) ABSTRACT

A valve unit is switchable to an open position at which an outside of an exterior portion and an inner cavity communicate with each other and a closed position at which a communication between the outside of the exterior portion and the inner cavity is blocked in an endoscope. In the endoscope, an electric power is supplied to a drive force generation section only when a connection portion of an universal cord is connected to a peripheral device, and the drive force generation section generates a drive force to drive the valve unit by a supply of the electric power. The valve unit moves from the closed position to the open position by the drive force generated by the drive force generation section.

12 Claims, 8 Drawing Sheets

(51) Int. Cl.
*A61B 1/12* (2006.01)
*G02B 23/24* (2006.01)

(52) U.S. Cl.
CPC ...... *A61B 1/00114* (2013.01); *A61B 1/00126* (2013.01); *A61B 1/00128* (2013.01); *A61B 1/0661* (2013.01); *A61B 1/121* (2013.01); *A61B 1/123* (2013.01); *G02B 23/2423* (2013.01); *G02B 23/2469* (2013.01); *G02B 23/2476* (2013.01); *A61B 1/0669* (2013.01)

(58) Field of Classification Search
USPC .......................................... 600/132–133, 159
See application file for complete search history.

(56) References Cited

U.S. PATENT DOCUMENTS

| | | | | |
|---|---|---|---|---|
| 4,862,872 A | * | 9/1989 | Yabe | A61B 1/00057 600/133 |
| 5,634,880 A | * | 6/1997 | Feldman | A61B 1/00057 600/132 |
| 7,871,372 B2 | * | 1/2011 | Nishiie | A61B 1/121 600/101 |
| 9,622,647 B2 | * | 4/2017 | Cushner | A61B 1/00119 |

FOREIGN PATENT DOCUMENTS

| | | |
|---|---|---|
| JP | 2003-098442 A | 4/2003 |
| JP | 2004-033547 A | 2/2004 |
| JP | 2008-073182 A | 4/2008 |
| JP | 2009-000384 A | 1/2009 |

OTHER PUBLICATIONS

Jul. 14, 2015 International Search Report issued in Patent Application No. PCT/JP2015/063473.

* cited by examiner

ENDOSCOPE AND ENDOSCOPE SYSTEM

CROSS-REFERENCE TO RELATED APPLICATIONS

This is a Continuation Application of PCT Application No. PCT/JP2015/063473, filed May 11, 2015 and based upon and claiming the benefit of priority from prior Japanese Patent Application No. 2014-151974, filed Jul. 25, 2014, the entire contents of which are incorporated herein by reference.

BACKGROUND OF THE INVENTION

1. Field of the Invention

The present invention relates to an endoscope and an endoscope system in which the endoscope is used.

2. Description of the Related Art

In general, an endoscope is subjected to a cleaning processing by, for example, a cleaning liquid and a sterilization processing by, for example, heat sterilization (autoclave sterilization) after use, and is reused. When cleaning the endoscope, it is necessary to prevent the inflow of the cleaning liquid into an inner cavity formed inside an exterior portion of the endoscope. When a pressure difference is produced between the outside of the exterior portion (an operating room) and the inner cavity due to the sterilization, it is necessary to cause the outside of the exterior portion to communicate with the inner cavity before the start of use and keep the pressure (atmospheric pressure) outside the exterior portion and the pressure in the inner cavity uniform. If the pressure outside the exterior portion and the pressure in the inner cavity are uniform, the operation force amount of the endoscope is not great during the use of the endoscope, and the breakdown of the endoscope caused by the pressure difference is effectively prevented.

From the above perspective, the endoscope is provided with a valve unit to switch the communication state between the outside of the exterior portion and the inner cavity. The valve unit is switched to a closed position to block the communication between the outside of the exterior portion and the inner cavity at the time of cleaning. Before the start of the reuse of the endoscope after sterilization, the valve unit is switched to an open position at which the outside of the exterior portion and the inner cavity communicate with each other. For example, an endoscope in Jpn. Pat. Appln. KOKAI Publication No. 2000-157484 is provided with a cap attachment portion to which a sterilization cap is attached at the time of sterilization, and the valve unit is located in the vicinity of the cap attachment portion. In this case, the valve unit is kept at the closed position at the time of cleaning. The sterilization cap is attached to the cap attachment portion when sterilization is conducted, and the sterilization cap is detached from the cap attachment portion after the sterilization. When the sterilization cap is detached from the cap attachment portion, press force is applied to the valve unit from the sterilization cap, and the valve unit is switched from the closed position to the open position.

In an endoscope of Jpn. Pat. Appln. KOKAI Publication No. 2004-33547, the valve unit is provided in a light source connector (connection portion) of a universal cord. In an endoscope system in which this endoscope is used, a rod protruding toward the light source connector is provided in a light source unit (peripheral device) to which the light source connector is separably connected. Before the start of use after sterilization, the light source connector of the universal cord is connected to the light source unit. As a result, press force is applied to the valve unit from the rod, and the valve unit is switched from the closed position to the open position.

BRIEF SUMMARY OF THE INVENTION

According to one aspect of the invention, an endoscope used together with a peripheral device in an endoscope system, the endoscope including: an exterior portion which forms an exterior of the endoscope, and inside which an inner cavity is formed; a universal cord portion which includes a connection portion that is separably connected to the peripheral device, and which forms a part of the exterior portion; a valve unit switchable to an open position at which an outside of the exterior portion and the inner cavity communicate with each other and a closed position at which a communication between the outside of the exterior portion and the inner cavity is blocked; and a drive force generation section to which an electric power is supplied from the peripheral device only when the connection portion is connected to the peripheral device, and which is configured to generate a drive force to drive the valve unit by a supply of the electric power, the drive force generation section being configured to move the valve unit from the closed position to the open position by the drive force.

According to one another aspect of the invention, an endoscope system includes that: an endoscope which includes an exterior portion forming an exterior, an inner cavity being formed inside the exterior portion; a universal cord portion which includes a connection portion, and which forms a part of the exterior portion in the endoscope; a peripheral device to which the connection portion is separably connected; a valve unit provided in the endoscope, the valve unit being switchable to an open position at which an outside of the exterior portion and the inner cavity communicate with each other and a closed position at which a communication between the outside of the exterior portion and the inner cavity is blocked; a drive force generation section which is provided in the peripheral device, and which is configured to generate drive force by a supply of an electric power; and a connection receiving portion which receives the connection portion in the peripheral device, when the connection portion is connected to the connection receiving portion, the connection receiving portion locating the valve unit at a position at which the drive force generated in the drive force generation section is applied, and moving the valve unit from the closed position to the open position by the drive force.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

First Embodiment

Figure 1:
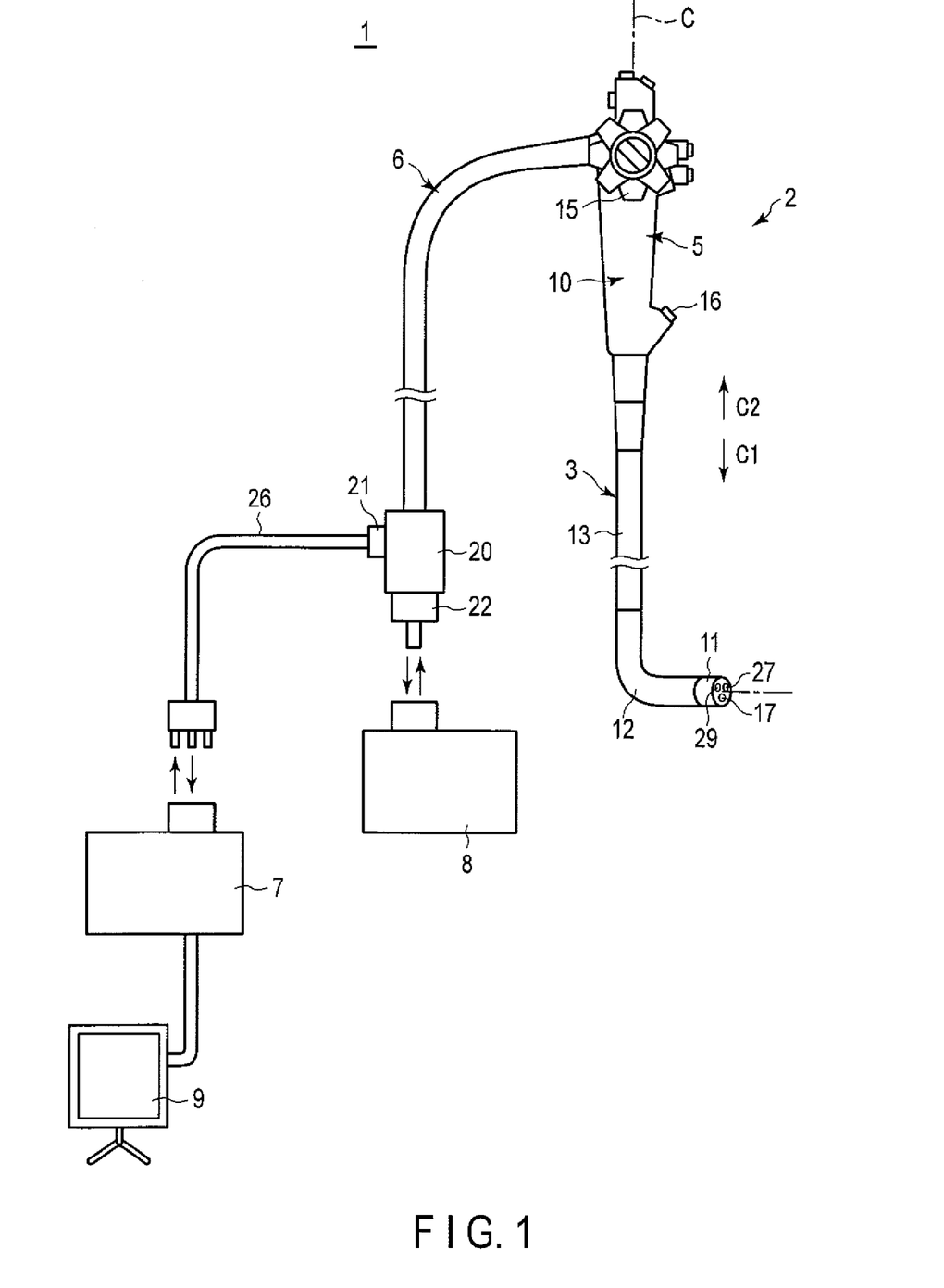
FIG. 1 is a schematic diagram showing an endoscope system according to a first embodiment.

A first embodiment of the present invention is described with reference to FIG. 1 to FIG. 6. FIG. 1 is a diagram showing an endoscope system 1. As shown in FIG. 1, the endoscope system 1 includes an endoscope 2. The endoscope 2 has a longitudinal axis C. Here, one of two directions parallel to the longitudinal axis C is a distal direction (a direction of an arrow C1 in FIG. 1), and a direction opposite to the distal direction is a proximal direction (a direction of an arrow C2 in FIG. 1).

As shown in FIG. 1, the endoscope 2 includes an insertion section 3 extending along the longitudinal axis C, and an operation section 5 provided on the proximal direction side with respect to the insertion portion 3. One end of a universal cord (universal cord portion) 6 is connected to the operation section 5. The exterior of the endoscope 2 including the insertion section 3, the operation section 5, and the universal cord 6 is formed by an exterior portion 10.

The endoscope system 1 includes an image processing unit (image processing device) 7 which is, for example, an image processor, a light source unit (light source device) 8, and a display unit (display device) 9 such as a monitor. In the present embodiment, peripheral devices of the endoscope 2 are constituted by the image processing unit 7, the light source unit 8, and the display unit 9, and the endoscope system 1 is constituted by the endoscope 2 and the peripheral devices. As peripheral devices, a suction source unit and a liquid supply source unit may be provided in addition to the image processing unit 7 and others.

The insertion section 3 includes a distal rigid portion 11 forming the distal end of the insertion section 3, a bending portion 12 provided on the proximal direction side with respect to the distal rigid portion 11, and a flexible tubular portion 13 provided on the proximal direction side with respect to the bending portion 12. The flexible tubular portion 13 extends along the longitudinal axis C between the operation section 5 and the bending portion 12. A bending operation knob 15 which is a bending operation section is provided in the operation section 5. A bending operation to bend the bending portion 12 is input in the bending operation knob 15. A treatment instrument insertion hole 16 is formed on the outer surface of the operation section 5. An opening 17 is formed in the distal face of the insertion section 3 (the distal surface of the distal rigid portion 11). A treatment instrument channel (not shown) extends through an inside of the operation section 5 and an inside of the insertion section 3, and the treatment instrument insertion hole 16 and the opening 17 are in communication with each other via the treatment instrument channel.

Figure 2:
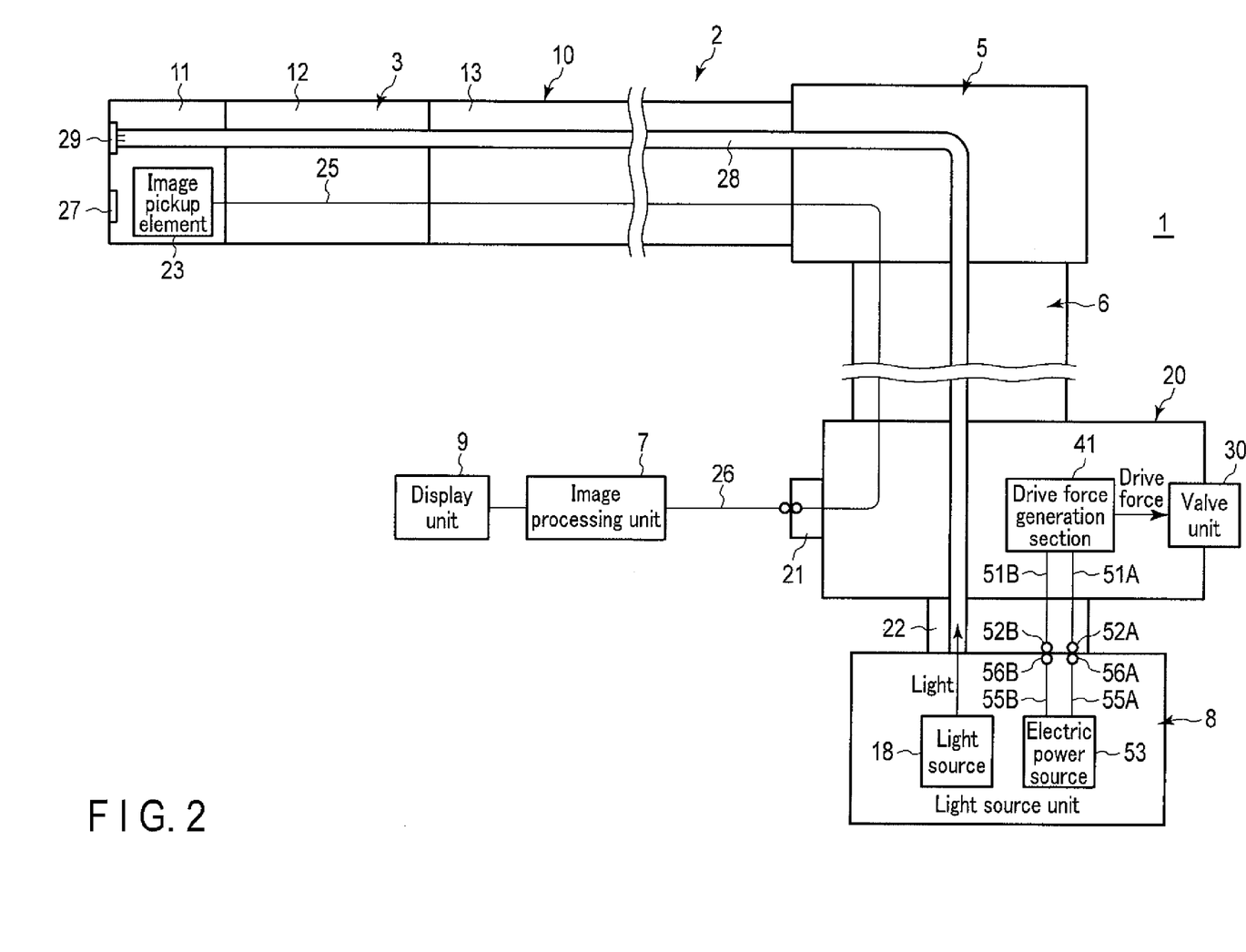
FIG. 2 is a schematic diagram showing an electric and optical connection state in the endoscope system according to the first embodiment.

FIG. 2 is a diagram showing an electric and optical connection state in the endoscope system 1. As shown in FIG. 1 and FIG. 2, a scope connector 20 is formed at the other end of the universal cord 6. The scope connector 20 includes a processor connection portion 21 which is separably connected to the image processing unit 7, and a light source connection portion (connection portion) 22 which is separably connected to the light source unit 8.

An image pickup element 23 is provided inside the distal hard portion 11. One end of an imaging cable (electric signal wire) 25 is connected to the image pickup element 23. The imaging cable 25 extends through the inside of the insertion section 3, the inside of the operation section 5, and an inside of the universal cord 6, and has the other end connected to the processor connection portion 21. When the processor connection portion 21 is connected to the image processing unit 7 via an external cable 26, the image processing unit 7 and the image pickup element 23 are electrically connected to each other. The image pickup element 23 images a subject from an observation window 27 provided on the distal face of the insertion section 3. An electric signal (imaging signal) based on the imaging is transmitted to the image processing unit 7 via the imaging cable 25 and the external cable 26. The image processing unit 7 generates an image of the subject on the basis of the transmitted electric signal, and displays the generated image on the display unit 9. Although one imaging cable 25 is shown in FIG. 2, more than one imaging cable (electric signal wire) 25 are connected to the image pickup element 23.

In the endoscope 2, a light guide 28 extends through the inside of the insertion section 3, the inside of the operation section 5, and the inside of the universal cord (universal cord portion) 6. The other end of the light guide 28 is connected to the light source connection portion 22. The light source unit 8 includes a light source 18 such as a lamp. When the light source connection portion 22 is connected to the light source unit (peripheral device) 8, the distal end (one end) of the light guide 28 is optically connected to the light source 18. The light emitted from the light source 18 is guided via the light guide 28. The light is then applied to the subject through an illumination window 29 provided on the distal surface of the insertion section 3.

As described above, in the endoscope system 1, the processor connection portion 21 of the universal cord 6 is connected to the image processing unit 7 via the external cable 26, and the light source connection portion 22 is connected to the light source unit 8, so that the subject is imaged, the light is applied to the subject, and the function as the endoscope 2 is performed.

Figure 3:
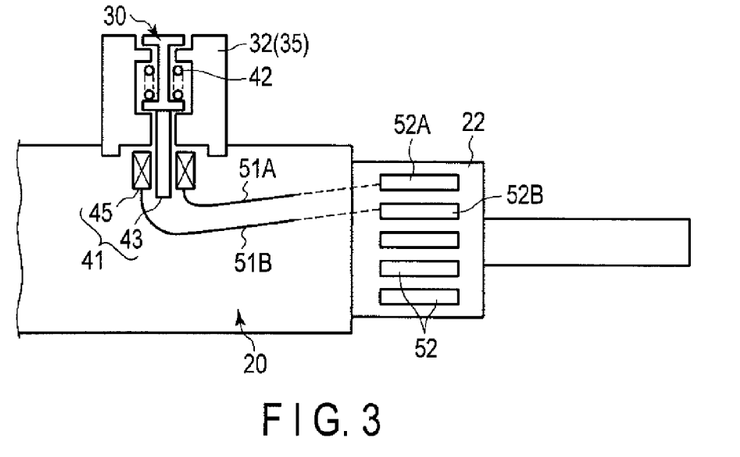
FIG. 3 is a schematic diagram showing the configuration of a scope connector of an endoscope according to the first embodiment.

FIG. 3 is a diagram showing the configuration of the scope connector 20. As shown in FIG. 2 and FIG. 3, a valve unit 30 and a drive force generation section 41 are attached to the scope connector 20 of the universal cord 6.

Figure 4:
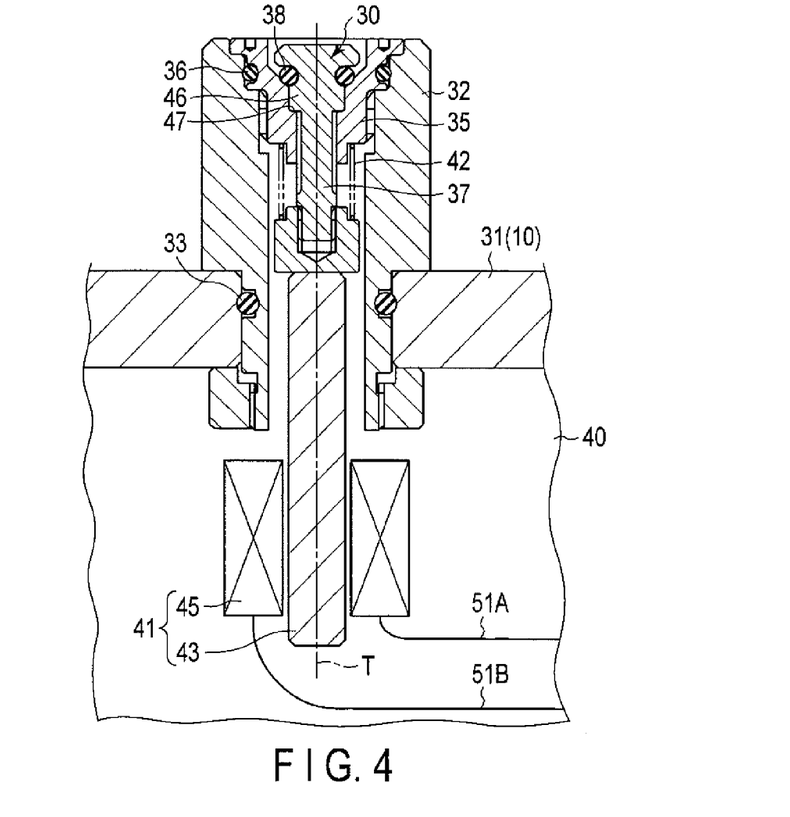
FIG. 4 is a sectional view schematically showing the configuration in the vicinity of a valve unit and a drive force generation section according to the first embodiment in a state in which no electric power is supplied to the drive force generation section and in which the pressure outside an exterior portion and the pressure in an inner cavity are uniform.
Figure 5:
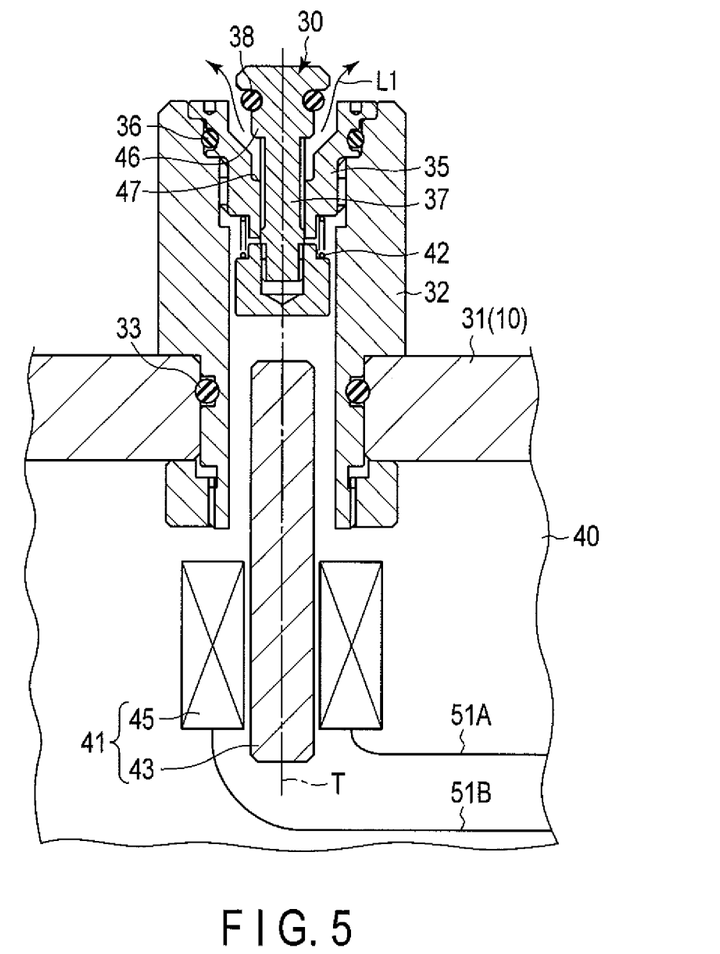
FIG. 5 is a sectional view schematically showing the configuration in the vicinity of the valve unit and the drive force generation section according to the first embodiment in a state in which no electric power is supplied to the drive force generation section and in which the pressure in the inner cavity is higher than the pressure outside the exterior portion.

FIG. 4 and FIG. 5 are diagrams showing the configuration in the vicinity of the valve unit 30 and the drive force generation section 41. As shown in FIG. 4 and FIG. 5, the scope connector 20 includes a connector exterior member 31 forming the exterior of the scope connector 20. The connector exterior member 31 is a part of the exterior portion 10 (see FIG. 1) forming the exterior of the endoscope 2. An inner cavity 40 is formed inside the exterior portion 10 including the connector exterior member 31. The inner cavity 40 is formed throughout the inside of the universal cord 6, the inside of the operation section 5, and the inside of the insertion section 3. Here, the space in which the imaging cable 25 extends is separated from the inner cavity 40 by a tube portion (not shown) covering the imaging cable 25, and is not in communication with the inner cavity 40. The treatment instrument channel (not shown) is separated from the inner cavity 40 by, for example, a channel tube (not shown), and is not in communication with the inner cavity 40. Therefore, the inner cavity 40 can only communicate with the outside of the exterior portion 10 (the outside of the endoscope 2) through the position at which the valve unit 30 is attached.

As shown in FIG. 4 and FIG. 5, a cylindrical support member 32 is fixed to the connector exterior member 31. The space between the support member 32 and the connector exterior member 31 is kept airtight and liquid-tight by a seal member 33. A cylindrical fixed member 35 is fixed to the support member 32. The fixed member 35 is inserted into the support member 32, and the space between the outer peripheral surface of the fixed member 35 and the inner peripheral surface of the support member 32 is kept airtight and liquid-tight by a seal member 36.

The valve unit 30 is attached to the connector exterior member 31 while being inserted into the support member 32 and the fixed member 35 from the outside of the exterior portion 10. The valve unit 30 includes a shaft portion 37, and a seal member 38 which is fixed to the outer peripheral surface of the shaft portion 37. The valve unit 30 including the shaft portion 37 and the seal member 38 is movable relative to the support member 32 and the fixed member 35 along a movement axis T. In the present embodiment, the movement axis T corresponds to the central axis of the shaft portion 37, and the fixed member 35 and the support member 32 are provided coaxially with the movement axis T. The movement axis T extends toward the inner cavity 40 from the outside of the exterior portion 10, and extends substantially perpendicularly to the outer surface of the connector exterior member 31.

Here, FIG. 4 shows a state in which the pressure outside the exterior portion 10 and the pressure in the inner cavity 40 are uniform or a state in which the pressure outside the exterior portion 10 is higher than the pressure in the inner cavity 40. FIG. 5 shows a state in which the pressure in the inner cavity 40 is higher than the pressure outside the exterior portion 10. In both FIG. 4 and FIG. 5, a later-described electric power is not supplied to the drive force generation section 41. The valve unit 30 is movable between a closed position (position in FIG. 4) and an open position (position in FIG. 5) along the movement axis T. That is, the valve unit 30 is switchable to the closed position and the open position.

As shown in FIG. 4, the seal member 38 is in abutment with the inner circumferential surface of the fixed member 35 when the valve unit 30 is located at the closed position. Thus, the space between the outer peripheral surface of the shaft portion 37 and the inner peripheral surface of the fixed member 35 is kept airtight and liquid-tight by the seal member 38. This blocks the communication between the outside of the exterior portion 10 and the inner cavity 40. In contrast, as shown in FIG. 5, when the valve unit 30 is located at the open position, the seal member 38 does not contact the inner peripheral surface of the fixed member 35. Thus, the outside of the exterior portion 10 and the inner cavity 40 communicate with each other.

Inside the support member 32, a cylindrical spring member (urging portion) 42 extends along the movement axis T. The spring member 42 is provided to be wound around the shaft portion 37. One end (outer side end) of the spring member 42 is connected to the fixed member 35, and the other end (inner side end) of the spring member 42 is connected to the shaft portion 37 of the valve unit 30. As shown in FIG. 4, the valve unit 30 is urged to be located at the closed position by the spring member 42. Therefore, when the pressure outside the exterior portion 10 and the pressure in the inner cavity 40 are uniform (i.e. when there is no pressure difference between the outside of the exterior portion 10 and the inner cavity 40), the valve unit 30 is urged by the spring member 42 to be kept at the closed position. When the pressure difference is smaller than the urging force of the spring member 42, the valve unit 30 is also kept at the closed position.

When the pressure in the inner cavity 40 is higher than the pressure outside the exterior portion 10 (i.e. when the pressure outside the exterior portion 10 is negative and the pressure in the inner cavity 40 is positive), the pressure which works toward the outer side in the valve unit 30 along the movement axis T is higher. Thus, the valve unit 30 moves from the closed position against the urging force of the spring member 42 due to the pressure from the inner cavity 40. In this instance, the spring member 42 is compressed, and the valve unit 30 moves toward the outer side along the movement axis T. Accordingly, the valve unit 30 is switched from the closed position to the open position. As a result of the switching of the valve unit 30 to the open position, the seal member 38 separates from the inner peripheral surface of the fixed member 35, and the outside of the exterior portion 10 and the inner cavity 40 communicate with each other. A gas then flows out from the high-pressure (positive-pressure) inner cavity 40 to the low-pressure (negative-pressure) outside of the exterior portion 10 (an arrow L1 in FIG. 5).

As shown in FIG. 4 and FIG. 5, the drive force generation section 41 includes a core member 43 made of a magnetic material, and a coil 45 wound around the outer peripheral surface of the core member 43. The core member 43 is provided coaxially with the movement axis T, and is movable relative to the coil 45 and the support member 32 along the movement axis T. When the electric power is supplied to the drive force generation section 41, an electric current flows through the coil 45. As a result, the core member 43 is magnetized, and an electromagnetic force is generated. That is, in the present embodiment, the drive force generation section 41 is an electromagnet which is configured to be magnetized by the supply of the electric power, and the electromagnetic force is generated as a drive force when the electric power is supplied to the drive force generation section 41. Moreover, in the present embodiment, the drive force generation section 41 is located inside the universal cord 6, and is located in the inner cavity 40.

When no drive force is generated in the drive force generation section 41 and the valve unit 30 is located at the closed position, one end (inner side end) of the shaft portion 37 is in abutment with one end (outer side end) of the core member 43.

A protrusion 46 protruding toward a direction away from the movement axis T is provided in the shaft portion 37 of the valve unit 30. The protrusion 46 is located on the inner side of the seal member 38, and supports the seal member 38. The fixed member 35 is provided with an abutment receiving portion 47 on which the protrusion 46 abuts when the valve unit 30 is located at the closed position. When the protrusion 46 of the valve unit 30 abuts on the abutment receiving portion (movement regulation portion) 47, the movement of the valve unit 30 from the closed position toward the inner side along the movement axis T is regulated.

When the pressure outside the exterior portion 10 is higher than the pressure in the inner cavity 40 (i.e. when the pressure outside the exterior portion 10 is positive and the pressure in the inner cavity 40 is negative), the pressure which works toward the inner side in the valve unit 30 along the movement axis T is higher. However, in the present embodiment, the movement of the valve unit 30 from the closed position toward the inner side along the movement axis T is regulated by the abutment receiving portion 47 of the fixed member 35. Thus, even when the pressure outside the exterior portion 10 is higher than the pressure in the inner cavity 40, the valve unit 30 does not move from the closed position and is kept at the closed position by the abutment receiving portion (movement regulation portion) 47.

As described above, the valve unit 30 is a check valve which moves from the closed position to the open position due to the pressure from the inner cavity 40 when the pressure in the inner cavity 40 is higher than the pressure outside the exterior portion 10 but which does not move from the closed position due to the external pressure when the pressure outside the exterior portion 10 is higher than the pressure in the inner cavity 40.

Figure 6:
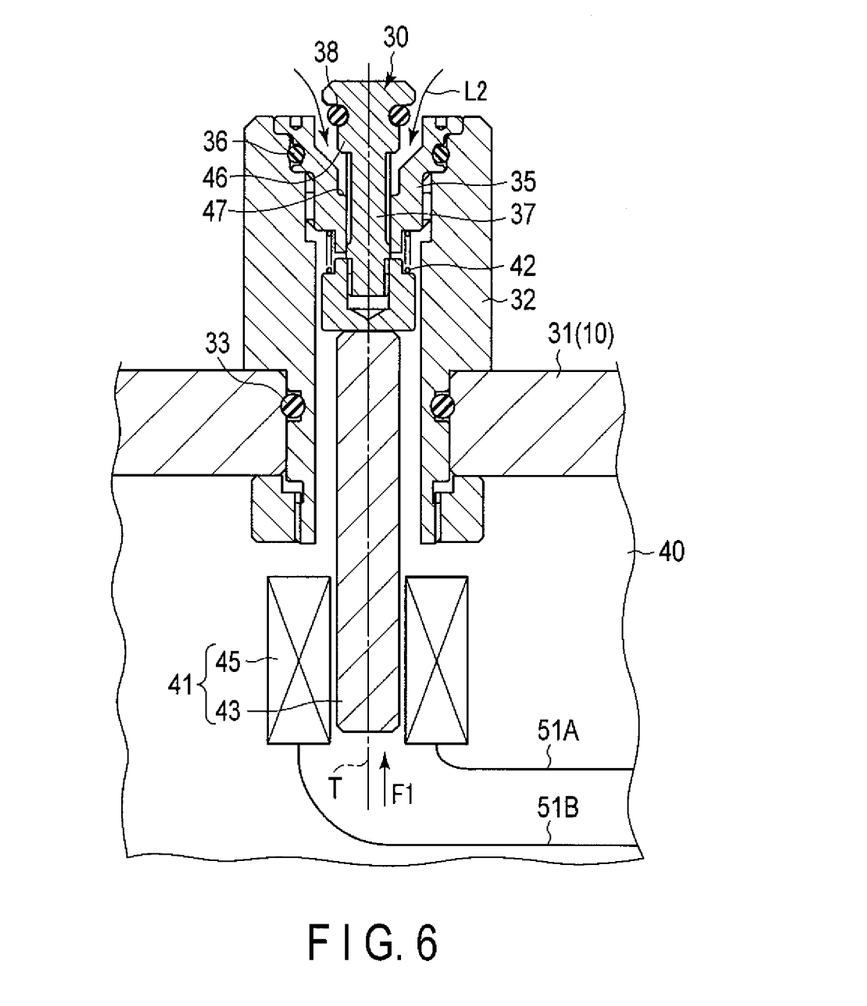
FIG. 6 is a sectional view schematically showing the configuration in the vicinity of the valve unit and the drive force generation section according to the first embodiment in a state in which an electric power is supplied to the drive force generation section.

FIG. 6 is a diagram showing the configuration in the vicinity of the drive force generation section 41 and the valve unit 30 in a state in which the electric power is supplied to the drive force generation section 41. FIG. 6 shows a state in which the pressure outside the exterior portion 10 is higher than the pressure in the inner cavity 40. As shown in FIG. 6, the electromagnetic force (drive force) F1 is generated toward the outer side in a direction along the movement axis T by the supply of the electric power to the drive force generation section 41. The core member 43 moves toward the outer side along the movement axis T by the electromagnetic force F1. As a result, the valve unit 30 located at the closed position is pressed toward the outer side by the core member 43. The valve unit 30 then moves to the outer side from the closed position along the movement axis T against the urging force of the spring member 42. Accordingly, the valve unit 30 is switched from the closed position to the open position. The direction of the electric current flowing through the coil 45 is adjusted so that the electromagnetic force F1 works toward the outer side.

When the drive force is generated in the drive force generation section 41, the valve unit 30 is switched to the open position regardless of the pressure outside the exterior portion 10 and the pressure in the inner cavity 40. That is, even when the pressure outside the exterior portion 10 is higher than the pressure in the inner cavity 40, the valve unit 30 moves to the outer side from the closed position along the movement axis T against the external pressure and the urging force of the spring member 42. Therefore, the sum of the pressure from the inner cavity 40 and the electromagnetic force is greater than the sum of the external pressure and the urging force of the spring member 42. As described above, in the present embodiment, even when the pressure outside the exterior portion 10 is higher than the pressure in the inner cavity 40, the valve unit 30 is switched from the closed position to the open position. As a result, a gas flows into the low-pressure (negative-pressure) inner cavity 40 from the high-pressure (positive-pressure) outside of the exterior portion 10 (an arrow L2 in FIG. 6).

As shown in FIG. 2 and FIG. 3, one end of each of first electric paths (scope side electric paths) 51A and 51B is connected to the coil 45 of the drive force generation section 41. Each of the first electric paths 51A and 51B is formed by, for example, an electric wire extending through an inside of the scope connector 20. A first electric contact (52A or 52B) is provided at the other end of each of the first electric paths 51A and 51B. Contact pins 52 are formed on the outer surface of the light source connection portion 22 of the scope connector 20. The first electric contact 52A is one of the contact pins 52, and the first electric contact 52B is one of the contact pins 52 different from the first electric contact 52A.

As shown in FIG. 2, an electric power source 53 which outputs an electric power to be supplied to the drive force generation section 41 is provided in the light source unit 8. The electric power source 53 is a power supply such as a battery. The electric power source 53 may be provided separately from the light source unit 8. The light source unit 8 is provided with second electric paths (device side electric paths) 55A and 55B connected at each of one ends to the electric power source 53. A second electric contact (56A or 56B) is provided at the other end of each of the second electric paths 55A and 55B.

When the light source connection portion (connection portion) 22 of the universal cord 6 is connected to the light source unit (peripheral device) 8, the first electric contact (scope side electric contact) 52A is connected to the second electric contact (device side electric contact) 56A, and the first electric contact 52B is connected to the second electric contact 56B. As a result, the electric power can be supplied to the drive force generation section 41 from the electric power source 53 through the first electric paths 51A and 51B and the second electric paths 55A and 55B, and the drive force to drive the valve unit 30 is generated in the drive force generation section 41 by the supply of the electric power to the drive force generation section 41 as described above.

When the light source connection portion (connection portion 22) of the universal cord 6 is not connected to the light source unit (peripheral device) 8, each of the first electric contacts 52A and 52B does not contact the corresponding second electric contact (56A or 56B). Thus, the electric power source 53 and the drive force generation section 41 are electrically disconnected from each other. Therefore, no electric power is supplied to the drive force generation section 41, and no electromagnetic force (drive force) is generated in the drive force generation section 41.

As described above, in the present embodiment, the electric power is supplied to the drive force generation section 41 and drive force is generated in the drive force generation section 41 only when the light source connection portion (connection portion) of the universal cord 6 is connected to the light source unit (peripheral device) 8.

Next, functions and advantageous effects of the endoscope 2 and the endoscope system 1 in the present embodiment are described. After the use of the endoscope 2, the endoscope 2 is cleaned by immersing the endoscope 2 in, for example, a cleaning liquid. The valve unit 30 is located at the open position during the use of the endoscope 2, so that when the endoscope 2 is cleaned after use, no pressure difference is produced between the outside of the exterior portion 10 (an operating room) and the inner cavity 40, and the pressure (atmospheric pressure) outside the exterior portion 10 and the pressure in the inner cavity 40 are uniform. After the use of the endoscope 2, the light source connection portion (connection portion 22) of the universal cord 6 is disconnected (separated) from the light source unit (peripheral device) 8. Thus, the first electric contact (52A or 52B) of each of the first electric paths 51A and 51B does not contact the second electric contact (56A or 56B) of the corresponding second electric path (55A or 55B). Therefore, when the endoscope 2 is cleaned, the electric power source 53 and the drive force generation section 41 are electrically disconnected from each other, so that no electric power is supplied to the drive force generation section 41, and no electromagnetic force (drive force) is generated in the drive force generation section 41.

As described above, the pressure (atmospheric pressure) outside the exterior portion 10 and the pressure in the inner cavity 40 are uniform, and no electromagnetic force is generated in the drive force generation section 41, so that the valve unit 30 is located at the closed position when the endoscope 2 is cleaned. Thus, the space between the shaft portion 37 (the valve unit 30) and the fixed member 35 is kept airtight and liquid-tight, and the inflow of the cleaning liquid into the inner cavity 40 from the outside of the exterior portion 10 is prevented. Accordingly, the attachment of the cleaning liquid to the inner objects (e.g. the imaging cable 25, the tube portion covering the imaging cable 25, and the light guide 28) extending in the inner cavity 40 can be effectively prevented.

In the cleaning processing of the endoscope 2, external force other than the endoscope system 1 such as water pressure (liquid pressure) from the cleaning liquid may be applied to the valve unit 30 toward the inner side. In the present embodiment, the movement of the valve unit 30 from the closed position toward the inner side along the movement axis T is regulated by the protrusion 46 and the abutment receiving portion (movement regulation portion) 47. Thus, even when the external force other than the endoscope system 1 is applied to the valve unit 30 toward the inner side, the valve unit 30 is kept at the closed position. Therefore, in the cleaning processing of the endoscope 2, the inflow of the cleaning liquid into the inner cavity 40 from the outside of the exterior portion 10 is further effectively prevented.

After the cleaning processing of the endoscope 2, a sterilization processing by, for example, heat sterilization (autoclave sterilization) is conducted. The sterilization treatment is conducted by disposing the endoscope 2 in a sterilization chamber. Temperature is higher in the sterilization chamber than in the operating room (atmosphere), and a sterilization gas is present inside the sterilization chamber. At the time of the sterilization processing, the light source connection portion (connection portion) 22 of the universal cord 6 is disconnected (separated) from the light source unit (peripheral device) 8. Therefore, no electromagnetic force (drive force) is generated in the drive force generation section 41 at the time of the sterilization processing.

In the sterilization treatment, the valve unit 30 moves toward the outer side from the closed position along the movement axis T when the pressure in the inner cavity 40 is higher than the pressure outside the exterior portion 10 (inside the sterilization chamber). Accordingly, the valve unit 30 is switched to the open position, and the gas flows out from the inner cavity 40 to the outside of the exterior portion 10. After the cleaning treatment and before the sterilization treatment, the pressure in the inner cavity 40 and the pressure (atmospheric pressure) in the operating room are substantially uniform as described above. Thus, when the gas flows out from the inner cavity 40 to the outside of the exterior portion 10 in the sterilization processing, the pressure in the inner cavity 40 becomes lower than the pressure in the operating room where the endoscope 2 is used.

In contrast, when the pressure outside the exterior portion 10 (inside the sterilization chamber) is higher than the pressure in the inner cavity 40, pressure is applied to the valve unit 30 toward the inner side from the outside of the exterior portion 10. However, in the present embodiment, the movement of the valve unit 30 from the closed position toward the inner side along the movement axis T is regulated by the abutment receiving portion (movement regulation portion) 47. Thus, even when the pressure outside the exterior portion 10 (inside the sterilization chamber) is higher than the pressure in the inner cavity 40 at the time of the sterilization processing, the valve unit 30 is kept at the closed position. Therefore, the inflow of the sterilization gas present inside the sterilization chamber into the inner cavity 40 is effectively prevented. Accordingly, the influence of the sterilization gas on the inner objects (e.g. the imaging cable 25, the tube portion covering the imaging cable 25, and the light guide 28) extending in the inner cavity 40 can be effectively prevented.

When the endoscope 2 which has been subjected to the sterilization processing is used, the light source connection portion (connection portion) 22 of the universal cord 6 is connected to the light source unit (peripheral device) 8. As a result, each of the first electric contacts 52A and 52B is connected to the corresponding second electric contact (56A or 56B), and the electric power can be supplied to the drive force generation section 41 from the electric power source 53 through the first electric paths 51A and 51B and the second electric paths 55A and 55B. The drive force to drive the valve unit 30 is generated in the drive force generation section 41 by the supply of the electric power to the drive force generation section 41. By the generated drive force, the valve unit 30 moves toward the outer side from the closed position along the movement axis T, and is switched to the open position.

As described above, the pressure (atmospheric pressure) in the operating room (outside the exterior portion 10) may become higher than the pressure in the inner cavity 40 due to the sterilization processing. However, in the present embodiment, the valve unit 30 is switched to the open position by the drive force (electromagnetic force) regardless of the pressure difference between the outside of the exterior portion 10 and the inner cavity 40. Thus, even when the pressure in the operating room (outside the exterior portion 10) becomes higher than the pressure in the inner cavity 40, the valve unit 30 is switched from the closed position to the open position by the drive force, and the gas flows into the low-pressure inner cavity 40 from the high-pressure outside of the exterior portion 10.

Therefore, even when a pressure difference is produced between the operating room (the outside of the exterior portion 10) and the inner cavity 40 due to the sterilization processing, the valve unit 30 moves to the open position by connecting the light source connection portion (connection portion) 22 of the universal cord 6 to the light source unit (peripheral device) 8. Thus, during the use of the endoscope 2, the pressure outside the exterior portion 10 and the pressure in the inner cavity 40 are uniform. Consequently, during the use of the endoscope 2, the operation force amount of the endoscope 2 does not become great, and the breakdown of the endoscope 2 caused by the pressure difference can be effectively prevented. No pressure difference is produced between the outside of the exterior portion 10 and the inner cavity 40 during the use of the endoscope 2, so that, for example, even when a hole which allows the inner cavity 40 to communicate with the outside is made in the insertion section 3 by a load, the inflow of, for example, blood and physiological saline into the inner cavity 40 is effectively prevented.

The connection of the light source connection portion 22 of the scope connector 20 of the universal cord 6 to the light source unit 8 is necessary to enable the function of the endoscope 2 to apply light to the subject through the illumination window 29. That is, before using the endoscope 2, the surgeon always connects the light source connection portion 22 to the light source unit 8. In the present embodiment, the electric power is supplied to the drive force generation section 41 only when the light source connection portion (connection portion) 22 is connected to the light source unit (peripheral device) 8, so that the electric power is supplied to the drive force generation section 41 during the use of the endoscope 2. Thus, at the time of the use of the endoscope 2 in which the light source connection portion 22 is connected to the light source unit 8, the drive force (electromagnetic force) to drive the valve unit 30 is surely generated in the drive force generation section 41, and the valve unit 30 can be surely switched from the closed position to the open position by the drive force.

Except during the use of the endoscope 2, for example, the cleaning processing and the sterilization processing, the light source connection portion 22 of the universal cord 6 is disconnected from the light source unit 8, so that no electric power is supplied to the drive force generation section 41 from the electric power source 53. Thus, except during the use of the endoscope 2, no drive force (electromagnetic force) is generated in the drive force generation section 41, and the valve unit 30 is surely prevented from being switched from the closed position to the open position by the drive force.

In the present embodiment, each of the first electric contacts 52A and 52B is connected to the corresponding second electric contact (56A or 56B) by connecting the light source connection portion (connection portion) 22 of the universal cord 6 to the light source unit (peripheral device) 8. Thus, it is not necessary for the surgeon to apply a great operation force amount in the operation to connect the light source connection portion 22 to the light source unit 8 and in the operation to connect each of the first electric contacts 52A and 52B to the corresponding second electric contact (56A or 56B). That is, the electric power can be supplied to the drive force generation section 41 and the valve unit 30 is switchable from the closed position to the open position by the easy operations that do not require a great operation force amount.

As described above, the present embodiment provides the endoscope 2 and the endoscope system 1 in which the valve unit 30 is not switched to the open position by the external force other than the endoscope system 1 and in which the valve unit 30 can be surely and easily switched from the closed position to the open position before the start of use after sterilization.

Modification of the First Embodiment

Although the drive force generation section 41 is an electromagnet formed from the core member 43 and the coil 45 in the first embodiment, it is not limited to this. For example, as shown in a modification in FIG. 7, the drive force generation section 41 may be provided with a motor 61 instead of the core member 43 and the coil 45. In the present modification, one end of each of first electric paths (scope side electric paths) 51A and 51B is connected to the motor 61. In the present modification as well as in the first embodiment, the electric power source 53 and the drive force generation section 41 (the motor 61) are electrically connected to each other and the electric power is supplied to the drive force generation section 41 only when the light source connection portion (connection portion) 22 of the universal cord 6 is connected to the light source unit (peripheral device) 8.

Figure 7:
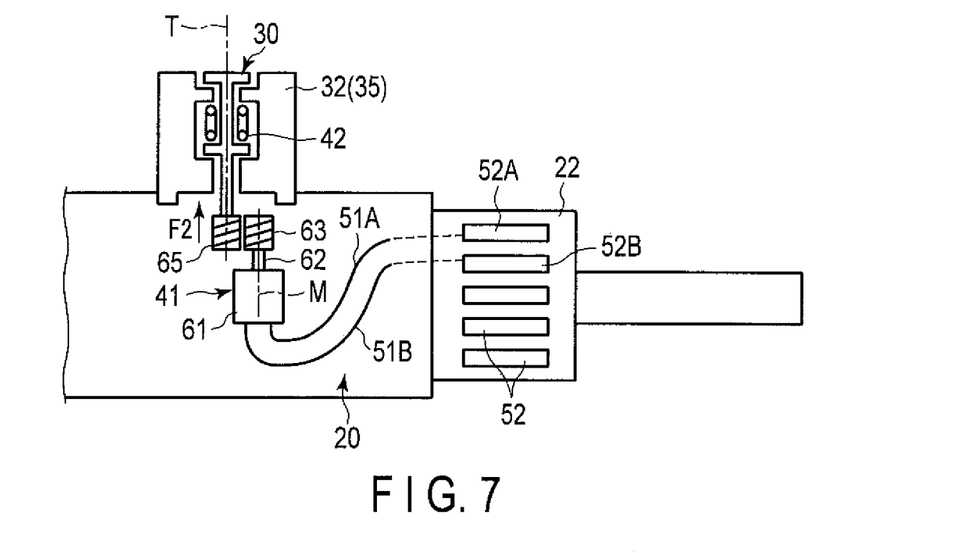
FIG. 7 is a schematic diagram showing the configuration of the scope connector of the endoscope according to a modification of the first embodiment.

In the present modification, when the motor 61 is driven by the electric power, a drive force to drive the valve unit 30 is generated. The motor 61 has a motor axis M, and a motor shaft 62 rotates around the motor axis M when the motor 61 is driven. A spiral body (motor side spiral body) 63 is fixed to the motor shaft 62. A spiral thread around the motor axis M is formed on the outer peripheral surface of the spiral body 63.

A spiral body (valve side spiral body) 65 is fixed to one end portion (inner side end portion) of the valve unit 30. A spiral thread around the movement axis T is formed on the outer circumferential surface of the spiral body 65. The outer peripheral surface of the spiral body 65 is in contact with the outer peripheral surface of the spiral body 63. In the configuration described above, the spiral body (motor side spiral body) 63 rotates together with the motor shaft 62 when the motor 61 is driven. As a result, a propulsive force F2 toward the outer side along the movement axis T is applied to the spiral body (valve side spiral body) 65 and the valve unit 30. When the propulsive force F2 toward the outer side is generated, the valve unit 30 and the spiral body 65 move from the closed position against the urging force of the spring member 42. In the present modification, the rotation direction of the motor shaft 62 of the motor 61 is adjusted and the direction of an electric current flowing through the motor 61 is adjusted so that the propulsive force F2 is applied toward the outer side.

As described above, in the present modification as well as in the first embodiment, a drive force (propulsive force) to drive the valve unit 30 is generated by the supply of the electric power to the drive force generation section 41. By the drive force, the valve unit 30 moves toward the outer side from the closed position along the movement axis T, and is switched to the open position.

Although the valve unit 30 is attached to the universal cord 6 and the drive force generation section 41 is provided inside the universal cord 6 in the first embodiment, it is not limited to this. For example, the valve unit 30 may be attached to the operation section 5, and the drive force generation section 41 may be located inside the operation section 5.

Although an electric power can be supplied to the drive force generation section 41 (the coil 45; the motor 61) by connecting the light source connection portion 22 of the universal cord 6 to the light source unit 8 in the above embodiments and others, it is not limited to this. For example, an electric power may be supplied to the drive force generation section 41 only when the processor connection portion (connection portion) 21 is connected to the image processing unit 7. The connection of the processor connection portion 21 of the universal cord 6 to the image processing unit 7 is necessary to enable the function of the endoscope 2 to image the subject through the observation window 27. That is, before using the endoscope 2, the surgeon always connects the processor connection portion 21 to the image processing unit 7. Therefore, at the time of the use of the endoscope 2, an electric power is supplied to the drive force generation section 41, and the valve unit 30 is surely switched from the closed position to the open position by the drive force generated in the drive force generation section 41.

In the first embodiment and its modification, the connection portion (21; 22) which is separably connected to the peripheral device (7; 8) used together with the endoscope (2) in the endoscope system (1) is provided in the universal cord (6) forming a part of the exterior portion (10). The valve unit (30) is switchable to the open position at which the outside of the exterior portion (10) and the inner cavity 40 communicate with each other and the closed position at which the communication between the outside of the exterior portion (10) and the inner cavity (40) is blocked. An electric power is supplied to the drive force generation section (41) only when the connection portion (21; 22) of the universal cord (6) is connected to the peripheral device (7; 8). In the drive force generation section (41), a drive force (F1; F2) to drive the valve unit (30) is generated by the supply of the electric power. The valve unit (30) moves from the closed position to the open position by the drive force (F1; F2) generated in the drive force generation section (41).

Second Embodiment

Next, a second embodiment of the present invention is described with reference to FIG. 8 and FIG. 9. In the second embodiment, the configuration in the first embodiment is modified as below. The same parts as those in the first embodiment have the same reference marks and are not described.

Figure 8:
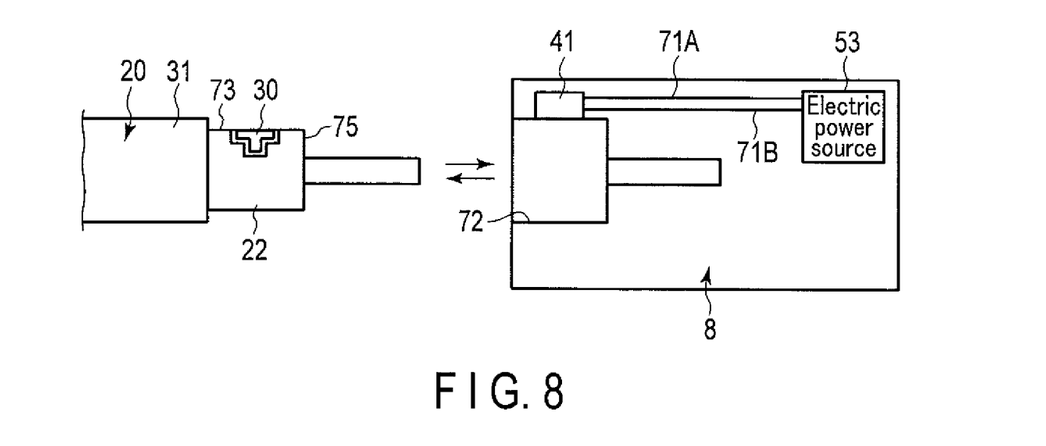
FIG. 8 is a schematic diagram showing the configurations of a scope connector of a universal cord and a light source unit according to a second embodiment in a state in which a light source connection portion is separated from the light source unit.
Figure 9:
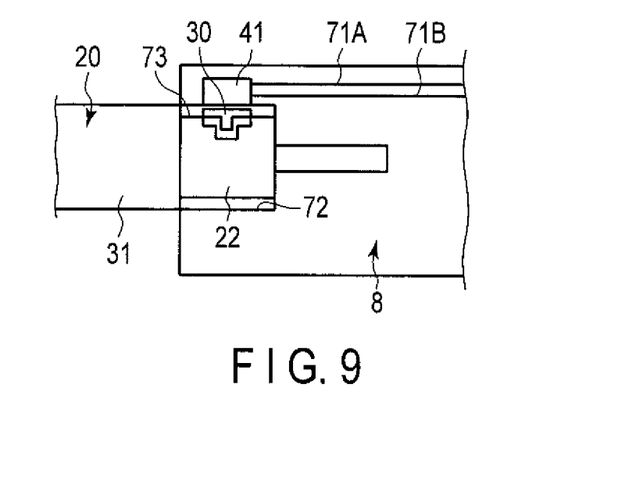
FIG. 9 is a schematic diagram showing the configurations of the scope connector of the universal cord and the light source unit according to the second embodiment in a state in which the light source connection portion is connected to the light source unit.

FIG. 8 and FIG. 9 are diagrams showing the configurations of the scope connector 20 of the universal cord 6 and the light source unit 8. FIG. 8 shows a state in which the light source connection portion 22 of the universal cord 6 is separated from the light source unit 8. FIG. 9 shows a state in which the light source connection portion 22 is connected to the light source unit 8. As shown in FIG. 8 and FIG. 9, in the present embodiment as well as in the first embodiment, the valve unit 30 is attached to the connector exterior member 31 of the scope connector 20. In the present embodiment, the valve unit 30 is located in an outer peripheral surface 73 of the light source connection portion (connection portion) 22.

In the present embodiment, the drive force generation section 41 is provided not in the endoscope 2 but in the light source unit (peripheral device) 8. The drive force generation section 41 is, for example, an electromagnet, and generates a drive force (electromagnetic force) by the supply of an electric power. The drive force generation section 41 and the electric power source 53 are always electrically connected to each other by electric paths 71A and 71B. Thus, while the light source unit 8 is active, the electric power is always supplied from the electric power source 53 to the drive force generation section 41. Therefore, while the light source unit 8 is active, the drive force (electromagnetic force) is always generated in the drive force generation section 41.

A depression 72 is formed in the light source unit 8. When the light source connection portion 22 is inserted in the depression 72, the light source connection portion 22 is separably connected to the light source unit 8. That is, the depression 72 serves as a connection receiving portion which receives the light source connection portion (connection portion) 22 in the light source unit (peripheral device) 8. As shown in FIG. 9, when the light source connection portion 22 is connected to the depression (connection receiving portion) 72, the valve unit 30 is located at a position to face the drive force generation section 41 (electromagnet). As a result, the valve unit 30 is located at a position at which the drive force (electromagnetic force) generated in the drive force generation section 41 is applied. In contrast, as shown in FIG. 8, when the light source connection portion 22 is not connected to the depression (connection receiving portion) 72 (i.e. when the light source connection portion 22 is separated from the depression 72), the valve unit 30 is located at a position at which the drive force generated in the drive force generation section 41 is not applied.

In the present embodiment as well, the valve unit 30 is switchable to the closed position and the open position. In the present embodiment as well, the valve unit 30 is urged to be located at the closed position by, for example, a spring member (urging portion) similar to the spring member 42 in the first embodiment. Thus, when the drive force generated in the drive force generation section 41 is not applied to the valve unit 30, the pressure in the inner cavity 40 is higher than the pressure outside the exterior portion 10, so that the valve unit 30 moves from the closed position to the open position due to the pressure from the inner cavity 40.

In the present embodiment as well, for example, a movement regulation portion similar to the protrusion 46 and the abutment receiving portion 47 in the first embodiment is provided to regulate the movement of the valve unit 30 from the closed position toward the inner side. Thus, when the drive force generated in the drive force generation section 41 is not applied to the valve unit, the valve unit 30 is kept at the closed position even if the pressure outside the exterior portion 10 is higher than the pressure in the inner cavity 40. That is, in the present embodiment as well, the valve unit 30 is a check valve which moves from the closed position to the open position due to the pressure from the inner cavity 40 when the pressure in the inner cavity 40 is higher than the pressure outside the exterior portion 10 but which does not move from the closed position due to the external pressure when the pressure outside the exterior portion 10 is higher than the pressure in the inner cavity 40.

When the light source connection portion 22 is connected to the depression 72 and the drive force generated in the drive force generation section 41 is applied to the valve unit 30, the valve unit 30 is switched from the closed position to the open position regardless of the pressure outside the exterior portion 10 and the pressure in the inner cavity 40.

That is, even when the pressure outside the exterior portion 10 is higher than the pressure in the inner cavity 40, the valve unit 30 moves toward the outer side from the closed position against the external pressure and the urging force of the spring member (42).

As described above, in the present embodiment, when the light source connection portion (connection portion) 22 of the universal cord 6 is connected to the depression (connection receiving portion) 72 of the light source unit (peripheral device) 8, the valve unit 30 is located at a position to receive the drive force generated in the drive force generation section 41. The valve unit 30 is then switched from the closed position to the open position by the drive force. Consequently, the present embodiment as well as the first embodiment provides the endoscope 2 and the endoscope system 1 in which the valve unit 30 is not switched to the open position by the external force other than the endoscope system 1 and in which the valve unit 30 can be surely and easily switched from the closed position to the open position before the start of use after sterilization.

Modification of the Second Embodiment

Figure 10:
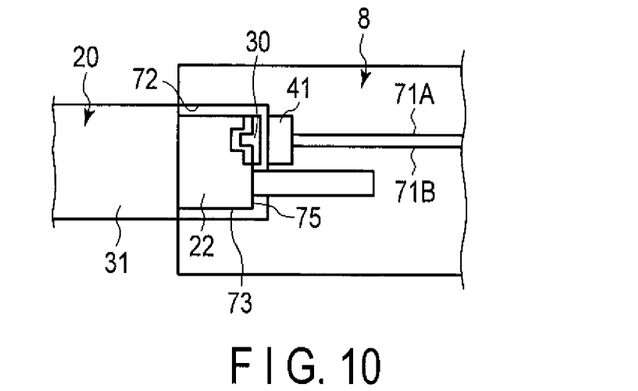
FIG. 10 is a schematic diagram showing the configurations of the scope connector of the universal cord and the light source unit according to a modification of the second embodiment in a state in which the light source connection portion is connected to the light source unit.

Although the valve unit 30 is provided in the outer peripheral surface 73 of the light source connection portion 22 in the second embodiment, it is not limited to this. For example, as shown in a modification in FIG. 10, the valve unit 30 may be provided in a connection end face 75 of the light source connection portion 22. In the present modification, the position of the valve unit 30 is changed from that in the second embodiment, the position of the drive force generation section 41 is also changed in the light source unit 8 from that in the second embodiment accordingly. In the present modification as well as in the second embodiment, when the light source connection portion 22 is connected to the depression (connection receiving portion) 72, the valve unit 30 is located at a position to face the drive force generation section 41 (electromagnet). As a result, the valve unit 30 is located at a position at which the electromagnetic force (drive force) generated in the drive force generation section 41 is applied. Although the valve unit 30 is movable along a direction that intersects at right angles with the direction in which the light source connection portion 22 is inserted into and removed from the depression (connection receiving portion) 72 in the second embodiment, the valve unit 30 is movable along the direction in which the light source connection portion 22 is inserted into and pulled out of the depression (connection receiving portion) 72 in the present modification.

The drive force generation section 41 is not limited to the electromagnet. For example, an electric motor may be provided instead of the electromagnet, and an electric power may be supplied to the electric motor to generate a drive force to drive the valve unit 30.

Although the valve unit 30 is located at a position at which the drive force generated in the drive force generation section 41 is applied by connecting the light source connection portion 22 of the universal cord 6 to the light source unit 8 in the second embodiment, it is not limited to this. For example, the valve unit 30 may be located at a position at which the drive force generated in the drive force generation section 41 is applied by connecting the processor connection portion (connection portion) 21 to the image processing unit 7. The connection of the processor connection portion 21 of the universal cord 6 to the image processing unit 7 is necessary to enable the function of the endoscope 2 to image the subject through the observation window 27. That is, before using the endoscope 2, the surgeon always connects the processor connection portion 21 to the image processing unit 7. Therefore, at the time of the use of the endoscope 2, a drive force is applied to the valve unit 30 from the drive force generation section 41, and the valve unit 30 is surely switched from the closed position to the open position by the drive force generated in the drive force generation section 41.

In the second embodiment and its modification, the connection portion (21; 22) which is separably connected to the peripheral device (7; 8) used together with the endoscope (2) in the endoscope system (1) is provided in the universal cord (6) forming a part of the exterior portion (10), and the connection receiving portion (72) which receives the connection portion (21; 22) is provided in the peripheral device (7; 8). The valve unit (30) is switchable to the open position at which the outside of the exterior portion (10) and the inner cavity (40) communicate with each other and the closed position at which the communication between the outside of the exterior portion (10) and the inner cavity (40) is blocked. In the drive force generation section (41) provided in the peripheral device (7; 8), a drive force to drive the valve unit (30) is generated by the generation of an electric power. When the connection portion (21; 22) of the universal cord (6) is connected to the connection receiving portion (72) of the peripheral device (7; 8), the valve unit (30) is located at a position at which the drive force generated in the drive force generation section (41) is applied, and the valve unit (30) moves from the closed position to the open position by the application of the drive force.

Referential Example

Next, a referential example is described with reference to FIG. 11. In the referential example, the same parts as those in the above embodiments and others have the same reference marks and are not described.

Figure 11:
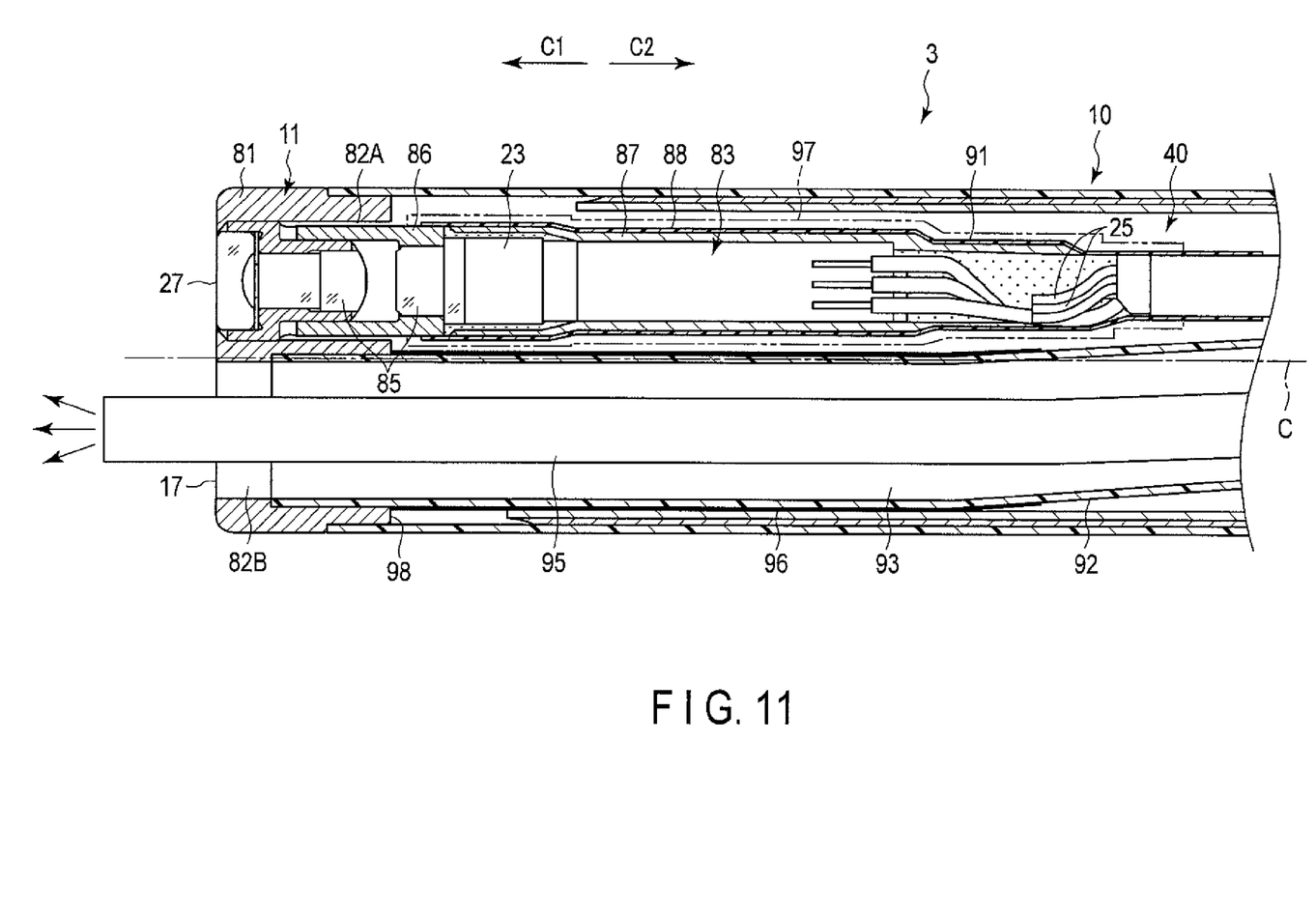
FIG. 11 is a sectional view schematically showing the configuration of the distal portion of an insertion section of the endoscope according to a referential example.

FIG. 11 is a diagram showing the configuration of the distal portion of the insertion section 3 of the endoscope 2. As shown in FIG. 11, in the present referential example as well, the insertion section 3 extends along the longitudinal axis C, and the inner cavity 40 is formed inside the insertion section 3 (inside the exterior portion 10).

A distal frame (rigid portion body) 81 forming the distal rigid portion 11 is provided in the insertion section 3. The distal face of the insertion section 3 is formed by the distal frame 81. Housing portions 82A and 82B passing through the distal frame 81 in a direction parallel to the longitudinal axis C are formed in the distal frame 81. The observation window 27 is formed at the distal end of the housing portion (first housing portion) 82A, and the opening 17 is formed at the distal end of the housing portion (second housing portion) 82B.

An imaging unit 83 extends in the inner cavity 40 from a proximal direction (a direction of an arrow C2 in FIG. 11) side toward a distal direction (a direction of an arrow C1 in FIG. 11) side. A lens 85 is housed in the housing portion 82A. The lens 85 is supported by a lens frame 86, and the lens frame 86 is fixed to the distal frame 81 in the housing portion 82A by adhesion. The imaging unit 83 is fixed to the lens 85 and the lens frame 86, for example, by adhesion. The imaging unit 83 is thereby coupled to the distal frame 81.

The imaging unit 83 includes the image pickup element 23, for example, a CCD which images the subject through the observation window 27. The image pickup element 23 is fixed to the lens 85 and the lens frame 86 by adhesion. The imaging unit 83 also includes a support member 87 in which the image pickup element 23 is housed. The image pickup element 23 is fixed to the support member 87 by adhesion. The outer peripheral surface of the support member 87 is covered with a tube portion 88. The distal ends of the support member 87 and the tube portion 88 are fixed to the lens frame 86. The tube portion 88 extends toward the proximal direction in the inner cavity 40.

One end of each of the imaging cables (electric signal wires) 25 is connected to the image pickup element 23. The imaging cables 25 extend toward the proximal direction through an inside of the tube portion 88. In the imaging unit 83, the exterior of the imaging unit 83 is formed by the outer surface of the tube portion 88. The outer surface of the tube portion 88 serves as a unit exposure surface 91 which is exposed in the inner cavity 40. Therefore, in the present referential example, no member to cover the unit exposure surface 91 of the imaging unit 83 is provided in the inner cavity 40.

A channel tube (channel member) 92 also extends from the proximal direction side toward the distal direction side in the inner cavity 40. The distal end of the channel tube 92 is fixed to the distal frame 81 by adhesion in the housing portion 82B. A channel (treatment instrument channel) 93 is formed inside the channel tube 92. The channel 93 is in communication with the opening 17 formed in the distal frame 81 via the housing portion 82B. A treatment instrument such as a laser probe 95 is inserted through the channel 93. When the treatment instrument is inserted through the channel 93, the treatment instrument protrudes from the opening 17 toward the distal direction. The outer surface of the channel tube (channel member) 92 is exposed in the inner cavity 40. Therefore, in the present referential example, no member to cover the outer surface of the channel tube 92 is provided in the inner cavity 40.

A light reflecting layer 96 which reflects light is provided on the outer surface of the channel tube 92. The light reflecting layer 96 serves as the outermost layer of the channel tube 92. The light reflecting layer 96 is formed in a range in which at least the image pickup element 23 is provided in the direction parallel to the longitudinal axis C. The light reflecting layer 96 is made of a material selected from the group consisting of aluminum, chromium, zinc, gold, silver, and nickel, and is made of a material which is high in light reflectivity at normal temperature (room temperature). The light reflecting layer 96 is preferably made of silver in particular. The light reflecting layer 96 is formed by vapor-depositing the above-mentioned material on the outer surface of the channel tube 92 through, for example, sputtering. In FIG. 11, the part of the outer surface of the channel tube 92 in which the light reflecting layer 96 is provided is indicated by, for example, a heavy line.

When the endoscope 2 is used, the laser probe 95 may be used as the treatment instrument in the channel (treatment instrument channel) 93. In this case, it is important to prevent laser light emitted from the distal end of the laser probe 95 from penetrating the channel tube 92 and the exterior of the imaging unit 83, and prevent the generation of flare resulting from the laser light in the image pickup element 23. In the present referential example, the light reflecting layer 96 is provided on the outer surface of the channel tube 92 which extends in parallel with the imaging element 83, and the light reflecting layer 96 is formed on the outer surface of the channel tube 92 in the range in which at least the image pickup element 23 is located in the direction parallel to the longitudinal axis C. Therefore, the laser light emitted from the laser probe 95 is reflected by the light reflecting layer 96 toward the inside of the channel tube 92. This prevents the laser light from traveling toward the image pickup element 23 from the channel tube 92, and can effectively prevent the generation of the flare in the image pickup element 23.

The outer surface of the imaging unit 83 is covered with a metallic frame member 97 indicated by a two-dot chain line in FIG. 11 to prevent the laser light from traveling toward the image pickup element 23 from the outer surface of the imaging unit 83. However, when the frame member 97 is provided, it is necessary to secure a space to dispose the frame member 97, and enlarge the inner cavity 40 at the distal portion of the insertion section 3. This increases the diameter (outside diameter) of the distal portion of the insertion section 3. On the contrary, in the present referential example, the laser light is prevented from traveling toward the image pickup element 23 without the provision of the frame member 97. Therefore, the distal portion of the insertion section 3 can be reduced in size. Here, in the configuration in which the frame member 97 is provided, the outer surface of the tube portion 88 (the outer surface of the imaging unit 83) is not exposed in the inner cavity 40.

Although the light reflecting layer 96 is formed on the outer surface of the channel tube 92 in the referential example described above, it is not limited to this. For example, in another referential example, the light reflecting layer (96) may be formed on the outer surface (the unit exposure surface 91) of the imaging unit 83. In this case as well, the light reflecting layer (96) is formed in the range in which at least the image pickup element 23 is located in the direction parallel to the longitudinal axis C. In yet another referential example, the light reflecting layer (96) may be provided on both the outer surface (the unit exposure surface 91) of the imaging unit 83 and the outer surface of the channel tube (channel member) 92.

In a certain referential example, the light reflecting layer (96) may be provided on at least one of the outer surface (the unit exposure surface 91) of the imaging unit 83 and the outer surface of the channel tube (channel member) 92, and the light reflecting layer (96) may be also formed on a proximal surface 98 of the distal frame 81.

In the above referential example and others, the imaging unit (83) and the channel member (92) extend from the proximal direction side toward the distal direction side in the inner cavity (40), and the imaging unit (83) includes the image pickup element (23) which is configured to image the subject through the observation window (27). The exterior of the imaging unit (83) is formed by the unit exposure surface (91) exposed in the inner cavity (40). The channel (93) which communicates with the opening (17) is formed inside the channel member (92). The light reflecting layer (96) which is configured to reflect light is formed on at least one of the unit exposure surface (91) of the imaging unit (83) and the outer surface of the channel member (92) in the range in which at least the image pickup element (23) is provided in the direction parallel to the longitudinal axis (C).

Characteristic matters of the referential example are additionally described below.

(Additional Note 1)

An endoscope comprising:

an insertion section which extends along a longitudinal axis, and inside which an inner cavity is formed, an observation window and an opening being formed in a distal portion of the insertion section;

an imaging unit extending from a proximal direction side toward a distal direction side in the inner cavity, the imaging unit including an image pickup element which is configured to image a subject through the observation window, and a unit exposure surface which forms an exterior of the imaging unit and which is exposed in the inner cavity;
a channel member which extends from the proximal direction side toward the distal direction side in the inner cavity, and inside which a channel that communicates with the opening of the insertion section is formed; and
a light reflecting layer which is configured to reflect light, the light reflecting layer being provided on at least one of the unit exposure surface of the imaging unit and an outer surface of the channel member and being formed in a range in which at least the image pickup element is provided in a direction parallel to the longitudinal axis.

(Additional Note 2)

The endoscope according to Additional note 1, wherein the light reflecting layer is vapor-deposited on the unit exposure surface and/or the outer surface of the channel tube by sputtering.

(Additional Note 3)

The endoscope according to Additional note 1, wherein the light reflecting layer is made of a material selected from the group consisting of aluminum, chromium, zinc, gold, silver, and nickel.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscope used together with a peripheral device in an endoscope system, the endoscope comprising:
    an exterior portion which forms an exterior of the endoscope, and inside of which an inner cavity is formed;
    a connection portion which is separably connected to the peripheral device; and
    a valve unit which switches to an open state so that an open environment and the inner cavity communicate with each other, and which switches to a closed state so that a communication between the open environment and the inner cavity is blocked,
    wherein only when the connection portion is connected to the peripheral device, a drive force generated by a supply of an electric power from the peripheral device is applied to the valve unit, and thereby the valve unit is switched from the closed state to the open state.

2. The endoscope according to claim 1, further comprising a drive force generation section which is provided in the connection portion, and which is configured to generate the drive force to be applied to the valve unit by the supply of the electric power from the peripheral device.

3. The endoscope according to claim 2, further comprising a universal cord portion in which the connection portion is provided, and which forms a part of the exterior portion.

4. The endoscope according to claim 3, further comprising an urging portion which is configured to urge the valve unit to be in the closed state.

5. The endoscope according to claim 3, wherein in a state in which the drive force is not generated in the drive force generation section, the valve unit switches from the closed state to the open state due to pressure from the inner cavity when the pressure in the inner cavity becomes higher than the pressure outside the exterior portion, and
    in the state in which the drive force is not generated in the drive force generation section, the valve unit is kept in the closed state even when the pressure outside the exterior portion becomes higher than the pressure in the inner cavity.

6. The endoscope according to claim 3, wherein the valve unit is movable between a position in the open state and a position in the closed state along a movement axis extending toward the inner cavity from the outside of the exterior portion, and
    the drive force generation section moves the valve unit toward an outer side from the position in the closed state along the movement axis by the drive force, and switches the valve unit to the open state.

7. The endoscope according to claim 6, further comprising a movement regulation portion which is configured to regulate the movement of the valve unit from the position in the closed state toward an inner side along the movement axis.

8. The endoscope according to claim 7, wherein when the pressure in the inner cavity becomes higher than the pressure outside the exterior portion, the valve unit moves toward the outer side from the position in the closed state along the movement axis due to the pressure from the inner cavity, and is switched to the open state, and
    in a state in which the pressure outside the exterior portion is higher than the pressure in the inner cavity, the movement regulation portion is configured to regulate the movement of the valve unit from the position in the closed state toward the inner side along the movement axis due to the pressure from the outside of the exterior portion, and keeps the valve unit at the position in the closed state.

9. The endoscope according to claim 3, wherein the valve unit is attached to the universal cord portion, and
    the drive force generation section is located inside the universal cord portion.

10. The endoscope according to claim 3, wherein the drive force generation section includes an electromagnet which is magnetized by the supply of the electric power, and which is configured to generate an electromagnetic force as the drive force.

11. An endoscope system comprising:
    the endoscope according to claim 2; and
    the peripheral device to which the connection portion is separably connected, the peripheral device including an electric power source which is configured to output the electric power to be supplied to the drive force generation section.

12. The endoscope system according to claim 11, wherein the endoscope includes a first electric path which extends through an inside of the exterior portion, and which has one end connected to the drive force generation section, and
    the peripheral device includes a second electric path which has one end connected to the electric power source, the other end of the second electric path being connected to the other end of the first electric path to allow the electric power to be supplied to the drive force generation section from the electric power source when the connection portion is connected to the peripheral device.

* * * * *